US011591650B2

(12) United States Patent
Shishkin et al.

(10) Patent No.: US 11,591,650 B2
(45) Date of Patent: Feb. 28, 2023

(54) MASSIVELY MULTIPLEXED RNA SEQUENCING

(71) Applicants: THE BROAD INSTITUTE, INC., Cambridge, MA (US); MASSACHUSETTS INSTITUTE OF TECHNOLOGY, Cambridge, MA (US)

(72) Inventors: Alexander A. Shishkin, Cambridge, MA (US); Mitchell Guttman, Cambridge, MA (US); Christine F. Surka, Cambridge, MA (US); Eric Lander, Cambridge, MA (US)

(73) Assignees: THE BROAD INSTITUTE, INC., Cambridge, MA (US); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 0 days.

(21) Appl. No.: 16/834,933

(22) Filed: Mar. 30, 2020

(65) Prior Publication Data

US 2020/0232030 A1    Jul. 23, 2020

Related U.S. Application Data

(62) Division of application No. 14/774,648, filed as application No. PCT/US2014/027015 on Mar. 14, 2014, now Pat. No. 10,612,088.

(60) Provisional application No. 61/786,103, filed on Mar. 14, 2013.

(51) Int. Cl.
*C12Q 1/6874* (2018.01)
*C12Q 1/6869* (2018.01)
*C12Q 1/6806* (2018.01)

(52) U.S. Cl.
CPC ......... *C12Q 1/6874* (2013.01); *C12Q 1/6806* (2013.01); *C12Q 1/6869* (2013.01); *C12Q 2521/107* (2013.01); *C12Q 2525/191* (2013.01); *C12Q 2535/122* (2013.01); *C12Q 2563/179* (2013.01)

(58) Field of Classification Search
CPC .. C12Q 1/6874; C12Q 1/6869; C12Q 1/6806; C12Q 2525/191; C12Q 2563/179; C12Q 2521/107; C12Q 2535/122
See application file for complete search history.

(56) References Cited

U.S. PATENT DOCUMENTS

| | | |
|---|---|---|
| 5,427,930 A | 6/1995 | Birkenmeyer |
| 5,744,311 A | 4/1998 | Fraiser |
| 5,866,336 A | 2/1999 | Nazarenko |
| 6,025,134 A | 2/2000 | Sooknanan |
| 6,027,889 A | 2/2000 | Barany |
| 6,033,881 A | 3/2000 | Himmler |
| 8,574,864 B2 * | 11/2013 | Vaidyanathan ...... C12Q 1/6806 435/21 |
| 2011/0287412 A1 | 11/2011 | Landthaler |
| 2012/0028814 A1 * | 2/2012 | Toloue ................. C12Q 1/6869 506/2 |
| 2012/0058521 A1 | 3/2012 | Church |
| 2013/0005585 A1 * | 1/2013 | Anderson .............. C12N 15/10 506/2 |
| 2013/0137587 A1 | 5/2013 | Van Eijk |
| 2014/0051585 A1 * | 2/2014 | Prosen ................. B01J 19/0046 506/2 |
| 2015/0275267 A1 | 10/2015 | O'Neil |

FOREIGN PATENT DOCUMENTS

| | | |
|---|---|---|
| EP | 0320308 A2 | 6/1989 |
| WO | 9001069 A1 | 2/1990 |

OTHER PUBLICATIONS

Weiner and Slatko., Biotechniques, 44 (5), 701-704, (Year: 2008).*
Pankovics et al., Mol. Biotechnol. 57: 974-981, August (Year: 2015).*
International Preliminary Report on Patentability dated Sep. 24, 2015 for PCT/US2014/027015, dated Sep. 24, 2015, 7 pages.
International Search Report and Written Opinion dated Jul. 8, 2014 for PCT/US2014/027015, dated Jul. 8, 2014, 22 pages.
Bigby, et al., "The Usefulness of Induced Sputum in the Diagnosis of Pneumocystis caim Pneumonia in Patients with the Acquired Immunodeficiency Syndrome", American Review of Respiratory Disease, vol. 133, No. 4, Apr. 1, 1986, 515-518.

(Continued)

*Primary Examiner* — Cynthia B Wilder
(74) *Attorney, Agent, or Firm* — F. Brent Nix, Esq.; Johnson, Marcou, Isaacs & Nix, LLC (57) ABSTRACT

The disclosed invention is related to a universal strand-specific protocol for the sequencing preparation of all classes of RNA. The protocol allows for sequencing for dozens to more than thousands of samples simultaneously. Specifically, the disclosed invention is a method for parallel sequencing target RNA from samples from multiple sources while maintaining source identification. The method includes providing samples of RNA comprising target RNA from two or more sources; labeling, at the 3' end, the RNA from the two or more sources with a first nucleic acid adaptor that comprises a nucleic acid sequence that differentiates between the RNA from the two or more sources; reverse transcribing the two or more sources to create a single stranded DNA comprising the nucleic acid sequence that differentiates between the RNA from the two or more sources; amplifying the single stranded DNA to create DNA amplification products that comprise the nucleic acid sequence that differentiates between the RNA from the two or more sources; sequencing the DNA amplification products thereby parallel sequencing target RNA from samples from multiple sources while maintaining source identification.

11 Claims, 6 Drawing Sheets

(56) References Cited

OTHER PUBLICATIONS

Kovacs, et al., "Diagnosis of Pneumocystis Carinii Pneumonia: Improved Detection in Sputum with Use of Monoclonal Antibodies", New England Journal of Medicine, vol. 318, No. 10, Mar. 10, 1988, 589-593.
Ognibene, et al., "The Diagnosis of Pneumocystis Carinii Pneumonia in Patients with the Acquired Immunodeficiency Syndrome Using Subsegmental Bronchoalveolar Lavage", American Review of Respiratory Disease, vol. 129, No. 6, Jun. 1, 1984, 929-932.
Prokaryia, ThermoPhage Single-Stranded DNA Ligase [online], Jun. 4, 2014, 3 pages.
Schluger, et al., J. Exp. Med., vol. 176, 1992, 1327-33.
Van Nieuwerburg, "Quantitative Bias in Illumina TruSeq and a Novel Post Amplification Barcoding Strategy for Multiplexed DNA and Small RNA Deep Sequencing", PLoS One, vol. 6, No. 10, Oct. 2011, 1-6.

* cited by examiner

MASSIVELY MULTIPLEXED RNA SEQUENCING

CROSS-REFERENCE TO RELATED APPLICATION

This application is a divisional of prior U.S. patent application Ser. No. 14/774,648 filed Sep. 10, 2015, which is a National Stage application of International Application No. PCT/US2014/027015, filed Mar. 14, 2014, which claims the benefit of U.S. Provisional Application No. 61/786,103, filed Mar. 14, 2013. The entire contents of the above-identified applications are hereby fully incorporated herein by reference.

STATEMENT OF GOVERNMENT SUPPORT

This invention was made with government support under grant number 1DP5OD012190-01 awarded by the National Institutes of Health and grant number 1P50HG006193-01 awarded by National Human Genome Research Institute, National Institutes of Health. The government has certain rights in the invention.

FIELD OF THE DISCLOSURE

This disclosure relates to RNA sequencing and specifically to multiplex RNA sequencing and enhanced methods of the same.

BACKGROUND

Next-generation sequencing is rapidly becoming the method of choice for the analysis of RNA, such as for transcriptional profiling. In contrast to microarray technology, sequencing allows identification of novel transcripts and does not require preexisting knowledge of the sequence of the genome. In addition, unlike hybridization-based detection, the sequencing of RNA allows genome-wide analysis of transcription at single nucleotide resolution.

Despite progress, sequencing of specific strands of RNA remains cumbersome and expensive. What is needed is an inexpensive method of sequencing large numbers of RNA simultaneously in solution. The method must be rapid and easy to perform. Methods of simultaneously sequencing large numbers of RNA molecules would provide chemical screens of cell cultures to identify drugs of interest, tissue, blood and other biological sample bank screening. These methods further would allow screening of RNA from tissue in paraffin-blocks. These methods would also provide antibiotic screening to determine drug resistance in microorganisms. This disclosure meets that need.

SUMMARY OF THE DISCLOSURE

A universal method is disclosed for the sequencing preparation of all classes of RNA. The method allows for sequencing for dozens to more than thousands of samples simultaneously. Thus, disclosed is a method for parallel sequencing target RNA from samples from multiple sources while maintaining source identification. The disclosed method includes providing samples of RNA comprising target RNA from two or more sources and labeling, at the 3' end, the RNA from the two or more sources with a first nucleic acid adaptor that includes a nucleic acid sequence that differentiates between the RNA from the two or more sources. The 3' end labeled RNA is reverse transcribed to create a single stranded DNA comprising the nucleic acid sequence that differentiates between the RNA from the two or more sources. The resultant DNA is amplified to create DNA amplification products that comprise the nucleic acid sequence that differentiates between the RNA from the two or more sources. Finally sequencing the DNA amplification products identifies, in parallel, target RNA from samples from multiple sources while maintaining source identification. In some embodiments of the disclosed method, the 3' labeled RNA is pooled. Also disclosed are kits for carrying out the disclosed method.

The advantages of the disclosed method over current protocols includes, but is not limited to, a strand-specific sequencing of all classes of RNA from any species including eukaryotes and prokaryotes including total RNA, antibody-selected RNA, 5'DGE and 3'DGE selected fragments, polyA-selected RNA, cross-linked RNA fragments from human, bacteria, and fungi. The disclosed method also allows for sequencing of dozens to several thousands of independent RNA samples simultaneously. The disclosed inventions are very low cost and low time per sample compared to commercial kits. The full protocol can take as little as approximately 6 hours.

The foregoing and other features of this disclosure will become more apparent from the following detailed description of several embodiments, which proceeds with reference to the accompanying figures.

BRIEF DESCRIPTION OF SEQUENCES

The nucleic and amino acid sequences are shown using standard letter abbreviations for nucleotide bases, and three letter code for amino acids, as defined in 37 C.F.R. 1.822. If only one strand of each nucleic acid sequence is shown, the complementary strand is understood as included by any reference to the displayed strand. All sequence database accession numbers referenced herein are understood to refer to the version of the sequence identified by that accession number as it was available on the designated date.

DETAILED DESCRIPTION OF SEVERAL EMBODIMENTS

I. Summary of Terms

Unless otherwise noted, technical terms are used according to conventional usage. Definitions of common terms in molecular biology may be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710).

The singular terms "a," "an," and "the" include plural referents unless context clearly indicates otherwise. Similarly, the word "or" is intended to include "and" unless the context clearly indicates otherwise. The term "comprises" means "includes." In case of conflict, the present specification, including explanations of terms, will control.

To facilitate review of the various embodiments of this disclosure, the following explanations of specific terms are provided:

Amplification: To increase the number of copies of a nucleic acid molecule, such as a DNA according the disclosed methods. The resulting amplification products are called "amplicons." Amplification of a nucleic acid molecule refers to use of a technique that increases the number of copies of a nucleic acid molecule (including fragments).

An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. This cycle can be repeated. The product of amplification can be characterized by such techniques as electrophoresis, restriction endonuclease cleavage patterns, oligonucleotide hybridization or ligation, and/or nucleic acid sequencing.

Other examples of in vitro amplification techniques include quantitative real-time PCR; reverse transcriptase PCR (RT-PCR); real-time PCR (rt PCR); real-time reverse transcriptase PCR (rt RT-PCR); nested PCR; strand displacement amplification (see U.S. Pat. No. 5,744,311); transcription-free isothermal amplification (see U.S. Pat. No. 6,033,881, repair chain reaction amplification (see WO 90/01069); ligase chain reaction amplification (see European patent publication EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134) amongst others.

Binding or stable binding (of an oligonucleotide): An oligonucleotide, such as a probe or primer binds or stably binds to a target nucleic acid, such as a nucleic acid with a PCR primer tag, if a sufficient amount of the oligonucleotide forms base pairs or is hybridized to its target nucleic acid. Binding can be detected by either physical or functional properties.

Binding site: A region on a protein, DNA, or RNA to which other molecules stably bind.

Capture moieties: Molecules or other substances that when attached to a nucleic acid molecule, such as a DNA molecule, allow for the capture of the nucleic acid molecule through interactions of the capture moiety and something that the capture moiety binds to, such as a particular surface and/or molecule, such as a specific binding molecule that is capable of specifically binding to the capture moiety. In some examples, a capture moiety is a biotin, which can be captured by avidin and or streptavidin. In some embodiments, the capture moiety, such as biotin, is attached to nucleic acid sequence that is used to remove non-target RNA from a sample, such as rRNA.

Contacting: Placement in direct physical association, including both in solid or liquid form.

Control: A reference standard. A control can be a known value or range of values indicative of basal levels or amounts or present in a tissue or a cell or populations thereof. A control can also be a cellular or tissue control, for example a tissue from a non-diseased state and/or exposed to different environmental conditions. A difference between a test sample and a control can be an increase or conversely a decrease. The difference can be a qualitative difference or a quantitative difference, for example a statistically significant difference.

Covalently linked: Refers to a covalent linkage between atoms by the formation of a covalent bond characterized by the sharing of pairs of electrons between atoms. In one example, a covalent link is a bond between an oxygen atom and a phosphorous atom, such as phosphodiester bonds in the backbone of a nucleic acid strand.

Complementary: A double-stranded DNA or RNA strand consists of two complementary strands of base pairs. Complementary binding occurs when the base of one nucleic acid molecule forms a hydrogen bond to the base of another nucleic acid molecule. Normally, the base adenine (A) is complementary to thymidine (T) and uracil (U), while cytosine (C) is complementary to guanine (G). For example, the sequence 5'-ATCG-3' of one ssDNA molecule can bond to 3'-TAGC-5' of another ssDNA to form a dsDNA. In this example, the sequence 5'-ATCG-3' is the reverse complement of 3'-TAGC-5'.

Nucleic acid molecules can be complementary to each other even without complete hydrogen-bonding of all bases of each molecule. For example, hybridization with a complementary nucleic acid sequence can occur under conditions of differing stringency in which a complement will bind at some but not all nucleotide positions.

Detect: To determine if an agent (such as a signal or particular nucleic acid, such as a RNA) is present or absent. In some examples, this can further include quantification in a sample, or a fraction of a sample, such as a particular cell or cells within a tissue.

Detectable label: A compound or composition that is conjugated directly or indirectly to another molecule to facilitate detection of that molecule. Specific, non-limiting examples of labels include fluorescent tags, enzymatic linkages, and radioactive isotopes. In some examples, a label is attached to an antibody or nucleic acid to facilitate detection of the molecule the antibody or nucleic acid specifically binds.

DNA sequencing: The process of determining the nucleotide order of a given DNA molecule. Generally, the sequencing can be performed using automated Sanger sequencing (AB13730x1 genome analyzer), pyrosequencing on a solid support (454 sequencing, Roche), sequencing-by-synthesis with reversible terminations (ILLUMINA® Genome Analyzer), sequencing-by-ligation (ABI SOLiD®) or sequencing-by-synthesis with virtual terminators (HELISCOPE®).

In some embodiments, DNA sequencing is performed using a chain termination method developed by Frederick Sanger, and thus termed "Sanger based sequencing" or "SBS." This technique uses sequence-specific termination of a DNA synthesis reaction using modified nucleotide substrates. Extension is initiated at a specific site on the template DNA by using a short oligonucleotide primer complementary to the template at that region. The oligonucleotide primer is extended using DNA polymerase in the presence of the four deoxynucleotide bases (DNA building blocks), along with a low concentration of a chain terminating nucleotide (most commonly a di-deoxynucleotide). Limited incorporation of the chain terminating nucleotide by the DNA polymerase results in a series of related DNA fragments that are terminated only at positions where that particular nucleotide is present. The fragments are then size-separated by electrophoresis a polyacrylamide gel, or in a narrow glass tube (capillary) filled with a viscous polymer. An alternative to using a labeled primer is to use labeled terminators instead; this method is commonly called "dye terminator sequencing."

"Pyrosequencing" is an array-based method, which has been commercialized by 454 Life Sciences. In some embodiments of the array-based methods, single-stranded DNA is annealed to beads and amplified via EmPCR®. These DNA-bound beads are then placed into wells on a fiber-optic chip along with enzymes that produce light in the presence of ATP. When free nucleotides are washed over this chip, light is produced as the PCR amplification occurs and ATP is generated when nucleotides join with their complementary base pairs. Addition of one (or more) nucleotide(s) results in a reaction that generates a light signal that is recorded, such as by the charge coupled device (CCD) camera, within the instrument. The signal strength is proportional to the number of nucleotides, for example, homopolymer stretches, incorporated in a single nucleotide flow.

High throughput technique: Through a combination of robotics, data processing and control software, liquid handling devices, and detectors, high throughput techniques allows the rapid screening of potential reagents, conditions, or targets in a short period of time, for example in less than 24, less than 12, less than 6 hours, or even less than 1 hour.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide (or its analog) and the DNA, RNA, and or DNA-RNA hybrid target. The oligonucleotide or oligonucleotide analog need not be 100% complementary to its target sequence to be specifically hybridizable. An oligonucleotide or analog is specifically hybridizable when there is a sufficient degree of complementarity to avoid non-specific binding of the oligonucleotide or analog to non-target sequences under conditions where specific binding is desired. Such binding is referred to as specific hybridization.

Isolated: An "isolated" biological component (such as a protein, a nucleic RNA, for example target RNA) has been substantially separated or purified away from other biological components in the cell of the organism in which the component naturally occurs, for example, extra-chromatin DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids. It is understood that the term "isolated" does not imply that the biological component is free of trace contamination, and can include nucleic acid molecules that are at least 50% isolated, such as at least 75%, 80%, 90%, 95%, 98%, 99%, or even 100% isolated.

Nucleic acid (molecule or sequence): A deoxyribonucleotide, ribonucleotide or deoxyribonucleotide-ribonucleotide polymer including without limitation, cDNA, mRNA, genomic DNA, and synthetic (such as chemically synthesized) DNA or RNA or hybrids thereof. The nucleic acid can be double-stranded (ds) or single-stranded (ss). Where single-stranded, the nucleic acid can be the sense strand or the antisense strand. Nucleic acids can include natural nucleotides (such as A, T/U, C, and G), and can also include analogs of natural nucleotides, such as labeled nucleotides.

The major nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major nucleotides of RNA are adenosine 5'-triphosphate (ATP or A), guanosine 5'-triphosphate (GTP or G), cytidine 5'-triphosphate (CTP or C) and uridine 5'-triphosphate (UTP or U). Nucleotides include those nucleotides containing modified bases, modified sugar moieties, and modified phosphate backbones, for example as described in U.S. Pat. No. 5,866,336 to Nazarenko et al.

Examples of modified base moieties which can be used to modify nucleotides at any position on its structure include, but are not limited to: 5-fluorouracil, 5-bromouracil, 5-chlorouracil, 5-iodouracil, hypoxanthine, xanthine, acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N-6-sopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, methoxyarninomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-S-oxyacetic acid, 5-methyl-2-thiouracil, 3 -(3-amino-3-N-2-carboxypropyl) uracil, 2,6-diaminopurine and biotinylated analogs, amongst others.

Examples of modified sugar moieties which may be used to modify nucleotides at any position on its structure include, but are not limited to arabinose, 2-fluoroarabinose, xylose, and hexose, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof.

Primers: Short nucleic acid molecules, such as a DNA oligonucleotide, which can be annealed to a complementary target nucleic acid molecule by nucleic acid hybridization to form a hybrid between the primer and the target nucleic acid strand. A primer can be extended along the target nucleic acid molecule by a polymerase enzyme. Therefore, primers can be used to amplify a target nucleic acid molecule, wherein the sequence of the primer is specific for the target nucleic acid molecule, for example so that the primer will hybridize to the target nucleic acid molecule under very high stringency hybridization conditions.

The specificity of a primer increases with its length. Thus, for example, a primer that includes 30 consecutive nucleotides will anneal to a target sequence with a higher specificity than a corresponding primer of only 15 nucleotides. Thus, to obtain greater specificity, probes and primers can be selected that include at least 5, 10, 15, 20, 25, 30, 35, 40, 45, 50 or more consecutive nucleotides.

In particular examples, a primer is at least 15 nucleotides in length, such as at least 5 contiguous nucleotides complementary to a target nucleic acid molecule. Particular lengths of primers that can be used to practice the methods of the present disclosure include primers having at least 5, at least 10, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 45, at least 50, or more contiguous nucleotides complementary to the target nucleic acid molecule to be amplified, such as a primer of 5-60 nucleotides, 15-50 nucleotides, 15-30 nucleotides or greater.

Primer pairs can be used for amplification of a nucleic acid sequence, for example, by PCR, or other nucleic-acid amplification methods known in the art. An "upstream" or "forward" primer is a primer 5' to a reference point on a nucleic acid sequence. A "downstream" or "reverse" primer is a primer 3' to a reference point on a nucleic acid sequence. In general, at least one forward and one reverse primer are included in an amplification reaction. PCR primer pairs can be derived from a known sequence, for example, by using computer programs intended for that purpose such as Primer (Version 0.5,© 1991, Whitehead Institute for Biomedical Research, Cambridge, Mass.).

Methods for preparing and using primers are described in, for example, Sambrook et al. (1989) *Molecular Cloning: A Laboratory Manual,* Cold Spring Harbor, N.Y.; Ausubel et al. (1987) *Current Protocols in Molecular Biology,* Greene Publ. Assoc. & Wiley-Intersciences.

Probe: A probe comprises an isolated nucleic acid capable of hybridizing to a target nucleic acid. A detectable label or reporter molecule can be attached to a probe. Typical labels include radioactive isotopes, enzyme substrates, co-factors, ligands, chemiluminescent or fluorescent agents, haptens, and enzymes.

Methods for labeling and guidance in the choice of labels appropriate for various purposes are discussed, for example, in Sambrook et al., *Molecular Cloning: A Laboratory Manual,* Cold Spring Harbor Laboratory Press (1989) and Ausubel et al., *Current Protocols in Molecular Biology,* Greene Publishing Associates and Wiley-Intersciences (1987).

Probes are generally at least 5 nucleotides in length, such as at least 10, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50 at least 51, at least 52, at least 53, at least 54, at least 55, at least 56, at least 57, at least 58, at least 59, at least 60, or more contiguous nucleotides complementary to the target nucleic acid molecule, such as 50-60 nucleotides, 20-50 nucleotides, 20-40 nucleotides, 20-30 nucleotides or greater.

Polymerizing agent: A compound capable of reacting monomer molecules (such as nucleotides) together in a chemical reaction to form linear chains or a three-dimensional network of polymer chains. A particular example of a polymerizing agent is polymerase, an enzyme which catalyzes the 5' to 3' elongation of a primer strand complementary to a nucleic acid template. Examples of polymerases that can be used to amplify a nucleic acid molecule include, but are not limited to the *E. coli* DNA polymerase I, specifically the Klenow fragment which has 3' to 5' exonuclease activity, Taq polymerase, reverse transcriptase (such as HIV-1 RT), *E. coli* RNA polymerase, and wheat germ RNA polymerase II.

The choice of polymerase is dependent on the nucleic acid to be amplified. If the template is a single-stranded DNA molecule, a DNA-directed DNA or RNA polymerase can be used; if the template is a single-stranded RNA molecule, then a reverse transcriptase (such as an RNA-directed DNA polymerase) can be used.

Sample: A sample, such as a biological sample, that includes biological materials (such as nucleic acid and proteins, for example RNA) obtained from an organism or a part thereof, such as a plant, animal, bacteria, and the like. In particular embodiments, the biological sample is obtained from an animal subject, such as a human subject. A biological sample is any solid or fluid sample obtained from, excreted by or secreted by any living organism, including without limitation, single celled organisms, such as bacteria, yeast, protozoans, and amebas among others, multicellular organisms (such as plants or animals, including samples from a healthy or apparently healthy human subject or a human patient affected by a condition or disease to be diagnosed or investigated, such as cancer). For example, a biological sample can be a biological fluid obtained from, for example, blood, plasma, serum, urine, bile, ascites, saliva, cerebrospinal fluid, aqueous or vitreous humor, or any bodily secretion, a transudate, an exudate (for example, fluid obtained from an abscess or any other site of infection or inflammation), or fluid obtained from a joint (for example, a normal joint or a joint affected by disease, such as a rheumatoid arthritis, osteoarthritis, gout or septic arthritis). A sample can also be a sample obtained from any organ or tissue (including a biopsy or autopsy specimen, such as a tumor biopsy) or can include a cell (whether a primary cell or cultured cell) or medium conditioned by any cell, tissue or organ.

Specific Binding Agent: An agent that binds substantially or preferentially only to a defined target such as a protein, enzyme, polysaccharide, oligonucleotide, DNA, RNA, or a small molecule. In an example, a "capture moiety specific binding agent" is capable of binding to a capture moiety that is covalently linked to a DNA molecule.

A nucleic acid-specific binding agent binds substantially only to the defined nucleic acid, such as RNA, DNA or a RNA-DNA hybrid, or to a specific region within the nucleic acid.

Tissue: A plurality of functionally related cells. A tissue can be a suspension, a semi-solid, or solid. Tissue includes cells collected from a subject such as blood, cervix, uterus, lymph nodes, breast, skin, and other organs.

Under conditions that permit binding: A phrase used to describe any environment that permits the desired activity, for example conditions under which two or more molecules, such as nucleic acid molecules and/or protein molecules, can bind.

Suitable methods and materials for the practice or testing of this disclosure are described below. Such methods and materials are illustrative only and are not intended to be limiting. Other methods and materials similar or equivalent to those described herein can be used. For example, conventional methods well known in the art to which this disclosure pertains are described in various general and more specific references, including, for example, Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999. In addition, the materials, methods, and examples are illustrative only and not intended to be limiting.

II. Overview

Figure 1:
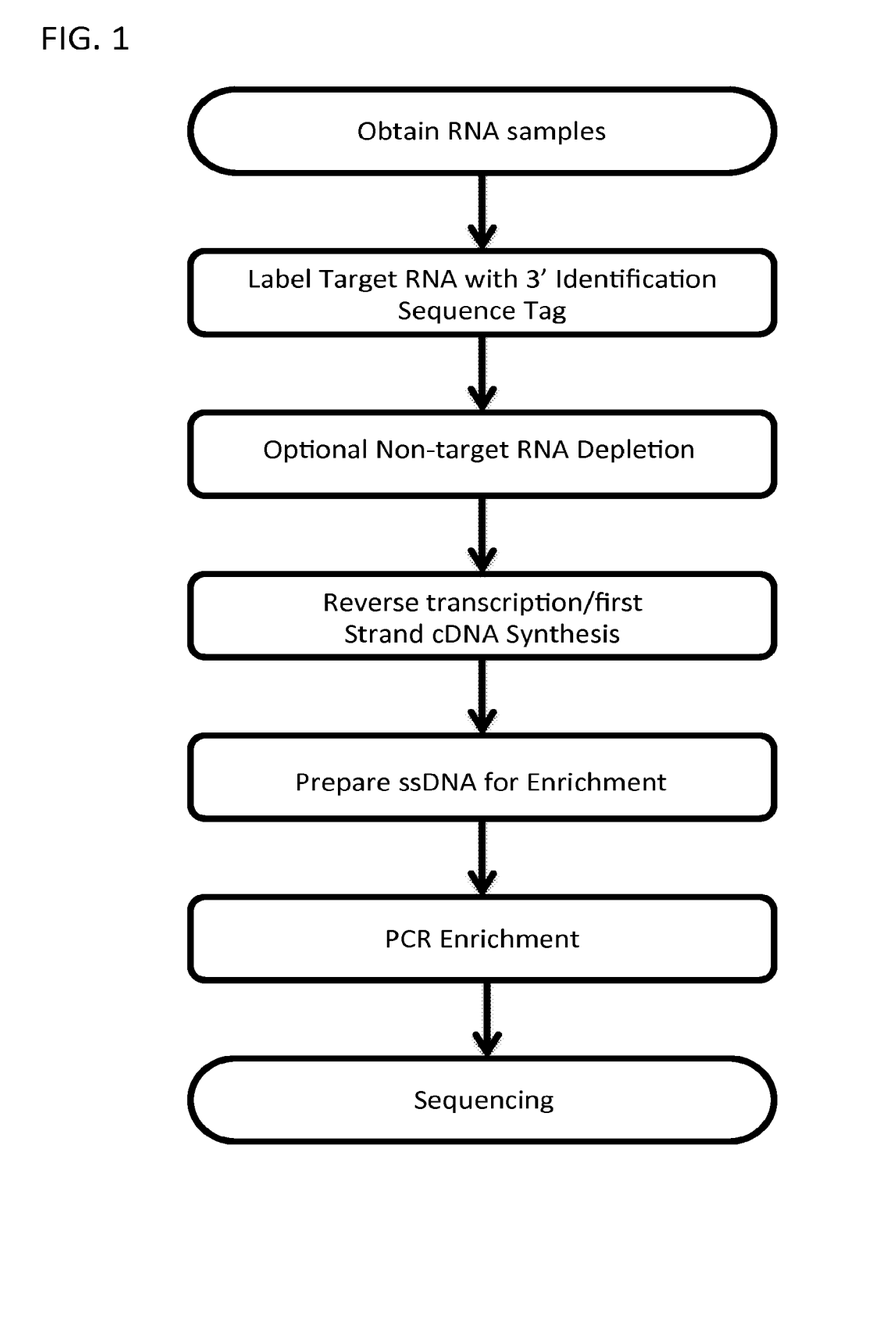
FIG. 1 is a schematic of an exemplary method of RNA sequencing as disclosed herein.

Disclosed herein is a novel method of identifying the sequence of a set of RNAs in a multiplex setting. FIG. 1 depicts a non-limiting example of the disclosed methods. As shown in FIG. 1, in the first step of the disclosed method, RNA is labeled (or barcoded) by attachment, such as ligation, of a 3' adaptor, which is typically coded to the source of the RNA, for example the specific sample. Optionally, one can perform oligo-based RNA depletion, such as depletion of rRNA, to remove RNA, which may interfere with the method or analysis. Once barcoded, individual samples of RNA can be pooled. The number of samples that can be pooled is only limited by the complexity of the barcodes, which is dictated by length, for example as the length of the barcode is increased by one nucleotide, the complexity of the barcode, or number of barcodes available is increased by 4. In the next step of the method, reverse transcription/first strand cDNA synthesis is performed with an adaptor-specific primer that specifically binds the 3' adaptor that has been attached to the RNA. During the reverse transcription/first strand cDNA synthesis information about the sequence of the RNA and the barcode is imprinted in the resulting ssDNA, thus locking in this information. The next step in the method is preparation of cDNA for enrichment. There are several ways that this can be accomplished. In one example, a second adapter ligation (ssDNA/ssDNA) by 3' linker ligation is performed. The adapter can be universal or can be barcoded, for example to increase the depth of multiplexing. In another example, $2^{nd}$ strand synthesis can be performed, for example to make a double stranded cDNA (ds cDNA). The now ds cDNA can then be end repaired, and in some examples dsDNA adapter ligated. In another example, the cDNA can be treated with a terminal transferase followed by isothermal amplification. The resulting DNA can be amplified, for example by PCR prior to sequence analysis. This enrichment effectively increases the signal of the sequencing.

Figure 2:
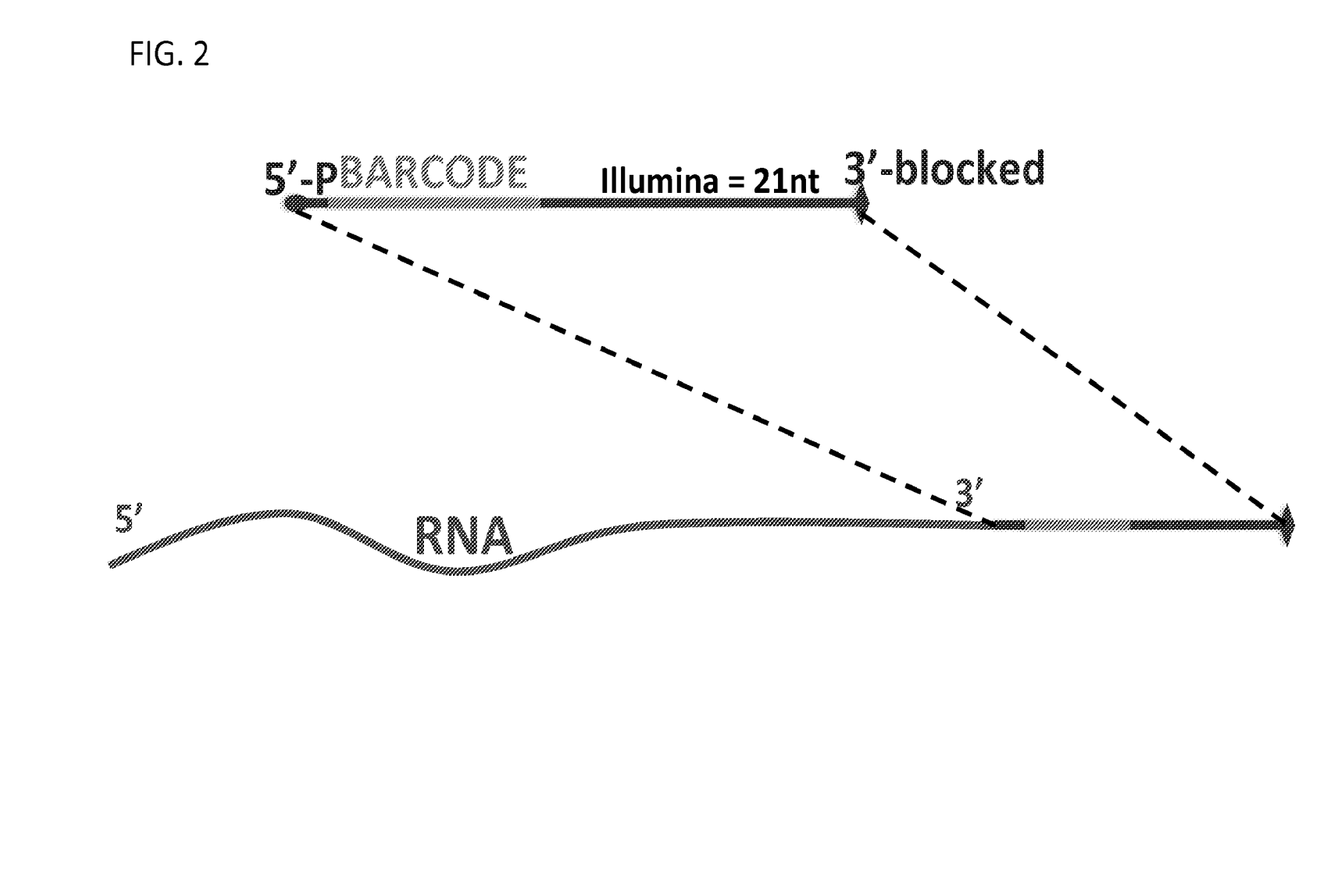
FIG. 2 is a schematic of 3' ligation of a sequence tag (barcode) to an RNA.

With reference to FIG. 2, as discussed above, in the first step of the disclosed method, there is a first ligation with a 3' adapter to label the RNA with a sequence label (barcode) that can be indexed to the origin or source of the sample. The adaptor can be RNA or DNA with preferably a 2 to 10 nucleotide barcode on the adaptor (or longer) with any modification (e.g., adenylation) which is compatible with a ligation reaction. In some embodiments, different adaptors with different barcodes are added to a single sample, such as a single well. For example, instead of adding a single unique barcode per sample, about 2 to about 10, such as 2, 3, 4 5, 6, 7, 8, 9, 10 or more, different adapters each containing a unique barcode sequence are added to each sample. It has been found that adding set of barcodes, such as between about 2-4 different adapters, each containing unique barcode sequence, increases ligation efficiency and experimental uniformity. In each set, each barcode is unique, and in all sets all barcode sequences are unique between each other.

Figure 3:
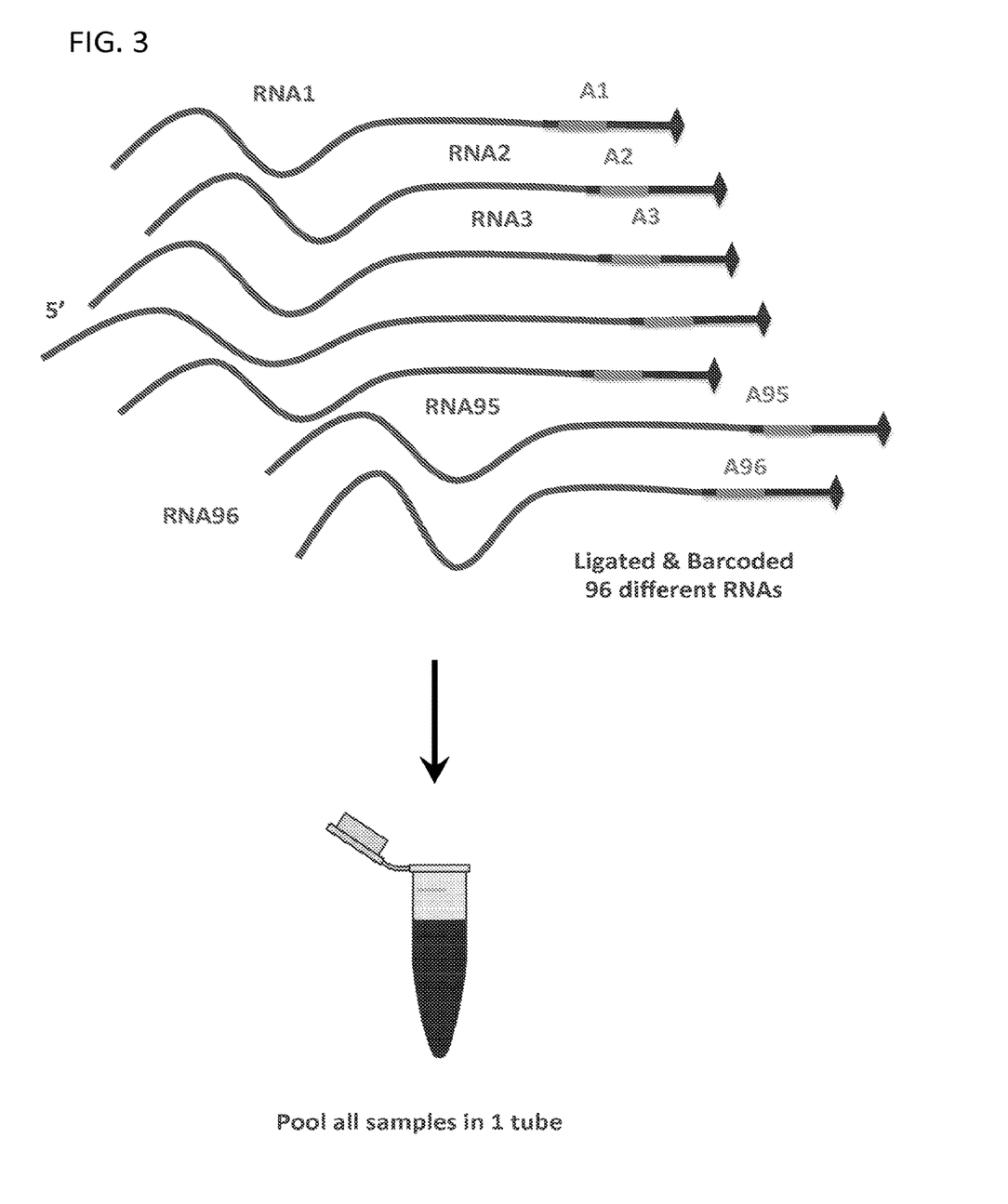
FIG. 3 is a schematic of the pooling of differently tagged (barcoded) RNA for subsequent processing

By way of example, if one considers samples in a 96 well plate (other larger or smaller formats are contemplated as well), one sample in one well would have 1 barcode (or a set of a few-to-several unique barcodes) and a second sample in a well would have a second barcode (or a second set of a few-to-several different unique barcodes) and so on, such that 96 samples would have 96 different barcodes (or 96 different unique barcodes sets) and 573 samples would have 573 different barcodes and the like. The sequences of the barcodes (which could be referred to as indexing sequences) are designed so that there is no self-ligation or cross ligation among the barcode sequences. FIG. 3 represents 96 ligated and barcoded different RNAs. The barcoded RNAs can then be pooled, as the information about the origin or source of the RNA in the sample is now set.

Figure 4:
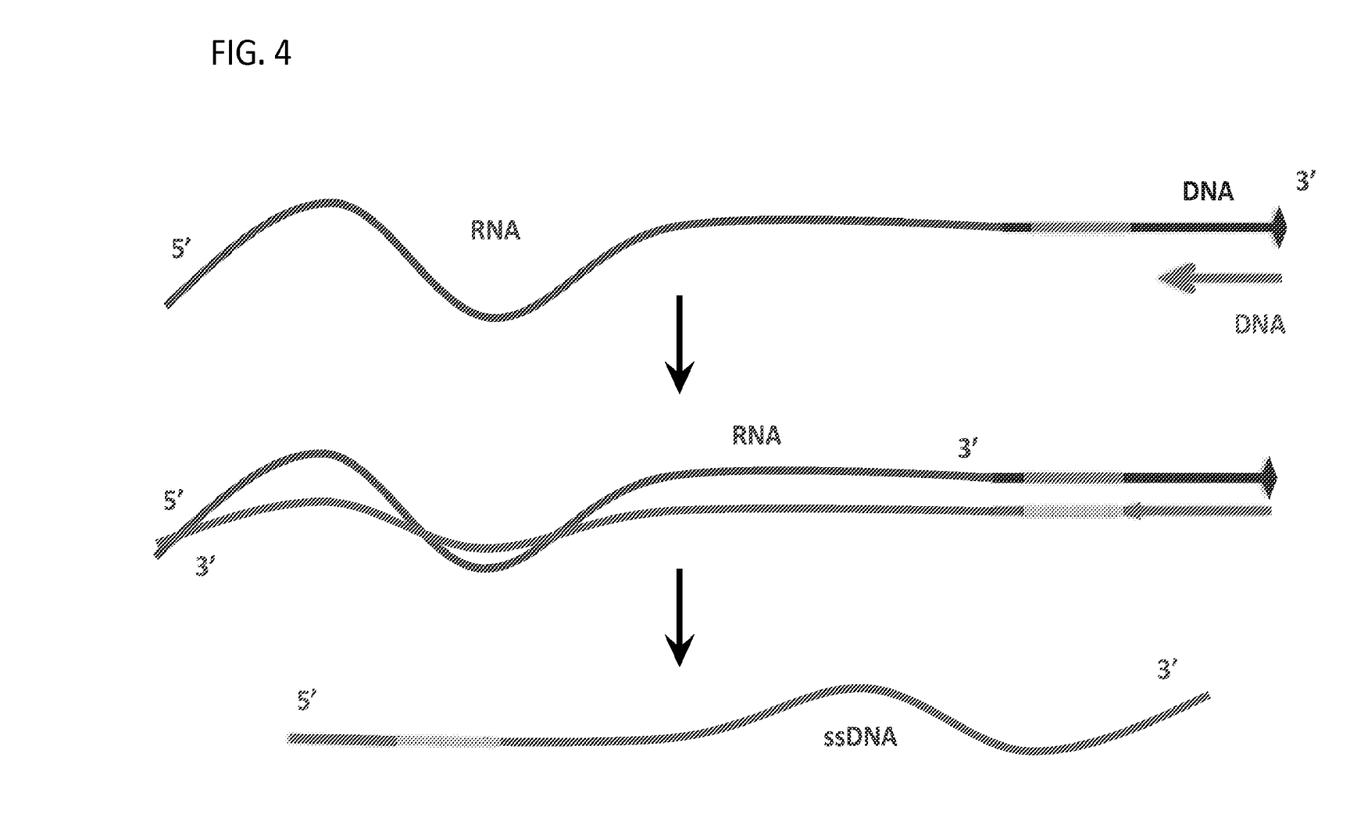
FIG. 4 is a schematic first strand ssDNA synthesis.

With reference to FIG. 4, in the next step, a reverse transcript of the RNA is generated using a primer specific to the adapter and a review transcriptase, such as a RNAseH-minus reverse transcriptase. This generates a ssDNA that encodes the RNA as well as the information about origin or source, in the form of the barcode. The primer and the RNA can be removed, such that they do not interfere with subsequent steps of the method and/or analysis. For example, the RT primer can be digested using ExoSAP, Exo I or any other ssDNA specific nuclease. The RNA can be degraded from the RNA/cDNA hybrid using NaOH, RNAseH or any other enzymatic or chemical method. In some examples, the resulting solution is cleaned up using Silane beads with low ethanol concentrations to remove the majority of leftover primers.

Figure 5:
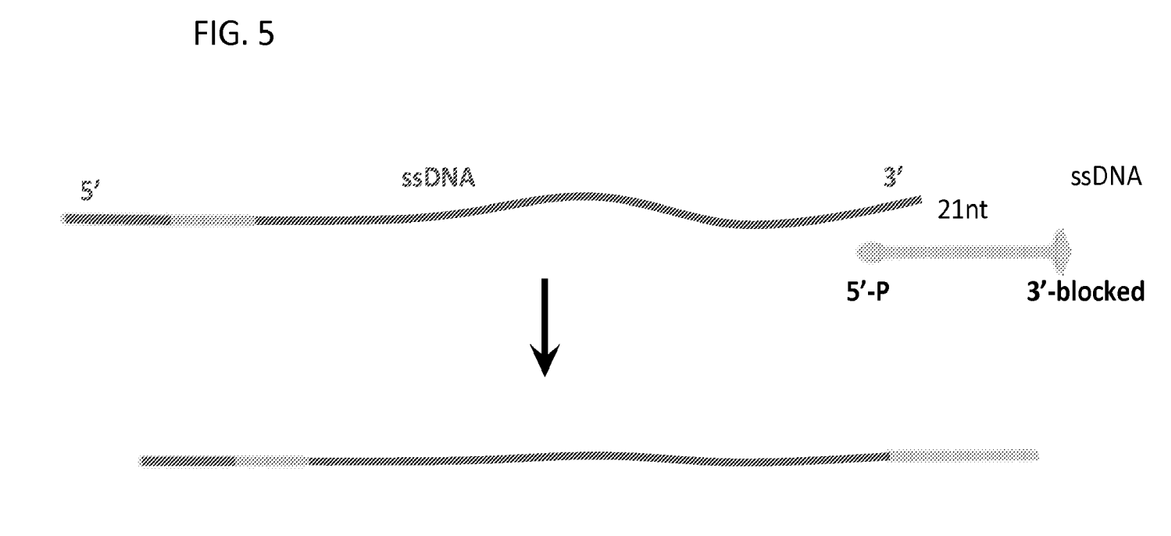
FIG. 5 is a schematic a second adapter ligation (ssDNA/ssDNA) by 3' linker ligation.

The next step in the method is preparation of ssDNA for enrichment. With reference to FIG. 5, in some embodiments of the disclosed method, a second adapter ligation (ssDNA/ssDNA) by 3' linker ligation is performed. The adapter can be universal or can be barcoded. The resultant nucleic acids can then be sequenced using any method of DNA sequencing available.

Figure 6:
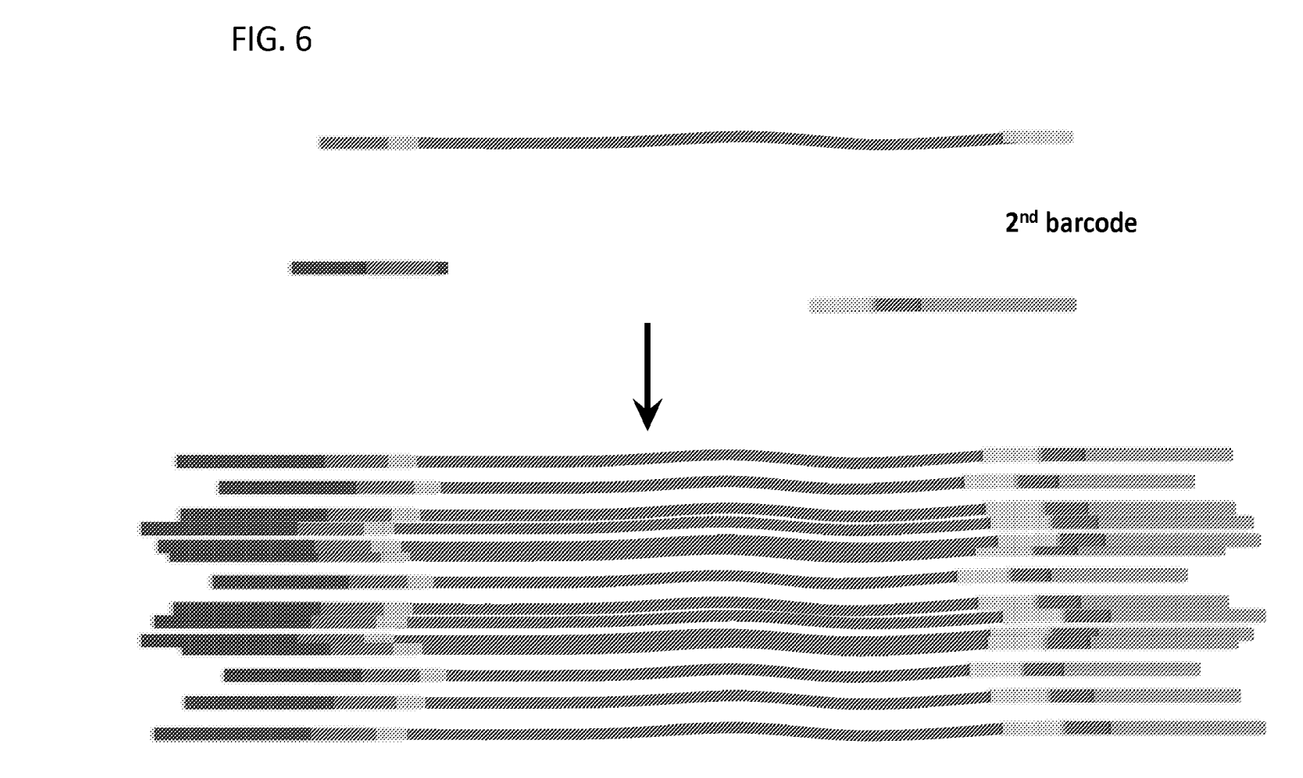
FIG. 6 is a schematic showing amplification of ssDNA encoding information about the origin of the target RNA.

With reference to FIG. 6, PCR enrichment of the RNA-seq library is performed. Any standard PCR polymerase can be used. For example Phusion® polymerase can be used under standard conditions. In some examples, the resultant PCR products are purified to remove primers, primer-dimers, short fragments, PCR polymerase, and nucleotides.

The 3' labeled RNA can optionally be pooled. The 3' end of single stranded DNA can be labeled with a second nucleic acid adaptor that comprises a site for binding of a PCR primer. The second nucleic acid adaptor can be a sequencing adaptor. In addition, the second nucleic acid adaptor can differentiate between single stranded DNA from two or more sources. Optionally, the sample can be depleted of non-target RNA by using one or more probes that specifically hybridize to the non-target RNA and wherein one or more probes comprise a label that facilitates the removal of the probe from the sample. The label includes, but is not limited to, biotin. It is to be understood that the first or second nucleic acid adaptor can be blocked at the 3' end. The first or second nucleic acid adaptor can be RNA, DNA or a RNA-DNA hybrid. The nucleic acid sequence that differentiates between the RNA or single stranded DNA from the two or more sources is preferably at least two nucleotides in length. Optionally, the reverse transcription primers are removed or degraded. The samples of different origins can be samples of the same cell type and/or tissue type that have been exposed to different environmental conditions, said conditions including, but not limited to, contacts with different test agents. The target RNA can be mRNA and the differences in expression of the mRNA are measured across samples from different sources. The disclosed invention further comprises quantifying the sequenced target RNAs of samples from multiple sources. The sequenced target RNAs can be sorted to their respective sources.

The benefits of the disclosed method include reduced costs. In addition, the disclosed method is a very efficient method for sequencing RNA biopsy material in paraffin-embedded blocks. The disclosed method is particularly useful for crosslinked RNA samples from cells and tissues. The disclosed method has been used in testing hundreds of poly-A selected samples, 5'-DGE, and 3'-DGE RNA samples. The disclosed method has been used in low complexity samples such as yeast or bacterial genomes where a small number of reads with deep multiplexing is required. The disclosed method allows for sequencing of dozens to thousands of RNA samples simultaneously.

III. Description of Several Embodiments

Disclosed is a method for parallel sequencing target RNA from samples (such as multiple target RNAs from multiple, for example one or more, samples) from multiple sources while maintaining source identification. The disclosed methods use a unique coding system to maintain the information about where a sample came from, so that a user, for example a laboratory worker, can keep track of the origin of a sample based on sequence information, such as that contained in a sequencing read of a nucleic acid sequencing system. The disclosed method includes providing samples of RNA, such as one or more, for example two or more samples of RNA, comprising target RNA from two or more sources. It is contemplated that the sources can be the same source, for example the same organism, at the same or different time points, for example when some one is looking at differences in RNA expression as a function of time or tissue, amongst others. In the disclosed method, the RNA is labeled at the 3' end (such as through a ligation reaction) with a first nucleic acid adaptor that comprises a nucleic acid sequence that differentiates between the RNA from the two or more sources. In other words, the RNA is tagged with a unique sequence identifier on the 3' end that distinguishes the RNA from one origin from an RNA of another origin, which in some examples can further include a site for binding of a PCR primer and/or a sequencing adaptor. The adaptor can be RNA and/or DNA and is about 2 to about 10 nucleotides is length, although longer are contemplated, for example the adaptor is about 2 to about 10 nucleotides in length, such as about 2, about 3, about 4, about 5, about 6, about 7, about 8, about 9, or about 10 nucleotides in length, such as about 2 to about 8, about 3 to about 10, about 5 to about 8 and the like. In some embodiments, the RNA is also labeled at the 5' end (such as through a ligation reaction) with a first 5' nucleic acid adaptor that comprises a nucleic acid sequence that differentiates between the RNA from the two or more sources, which in some examples can further include a site for binding of a PCR primer and/or a sequencing adaptor. The addition at the 5'-end of RNA can occur before or after the addition at the 3'-end. The labeled RNA (5' and/or 3') is reverse transcribed to create a single stranded DNA comprising the nucleic acid sequence that differentiates between the RNA from the two or more sources. In some examples the RNA is treated to block addition to the 3' end during the 5' ligation. In some embodiments, the single stranded RNA (such as the target RNA) can be labeled at the 3' end with a second nucleic acid adaptor that comprises a site for binding of a PCR primer. In some embodiments, the single stranded RNA (such as the target RNA) can be labeled at the 5' end with a second nucleic acid adaptor that comprises a site for binding of a PCR primer.

The single stranded DNA is amplified to create DNA amplification products that comprise the nucleic acid sequence that differentiates between the RNA from the two or more sources and the DNA amplification products are sequenced, thereby parallel sequencing target RNA from samples from multiple sources while maintaining source identification.

In some embodiments, the 3' labeled RNAs are pooled. For example, once the information about the origin of the RNA is locked in by the addition of the 3' label, the samples can be pooled and treated essentially identically for the remainder of whatever test, trial, or experiment is being conducted, as the information about the origin of the RNA can always be determined by the sequence. This gives the disclosed techniques the power to be used in multiplexing reactions, where one would want all the samples to be treated identically, which can be very important for experiments that rely on the analysis of the relative or absolute levels of RNA amongst multiple sources.

In some embodiments, the single stranded DNA can be labeled at the 3' end with a second nucleic acid adaptor that comprises a site for binding of a PCR primer. In some embodiments, the single stranded DNA can be labeled at the 5' end with a second nucleic acid adaptor that comprises a site for binding of a PCR primer. In some examples the second nucleic acid comprises a sequencing adaptor. In some embodiments, the second nucleic acid adaptor comprises a second nucleic acid sequence that can differentiate between single stranded DNA from two or more sources. In this way, the information about the origin can be further multiplexed. By way of example, this can be used to create a nested hierarchy about the origin of the RNA, for example, hierarchy by organism, tissue type, time point and so on, which allows all of the individual samples to be pooled and analyzed simultaneously. In some examples, the second nucleic acid adaptor comprises a site for binding of a PCR primer. In some embodiments, the single stranded DNA is pooled with single stranded DNA from one or more additional sources, wherein the single stranded DNA from one or more additional sources is similarly labeled.

In some embodiments, the samples are depleted of non-target RNA. By way of example, in a cellular system, much of the RNA in a sample, such as in a lysed sample is comprised of rRNA, which may not be of interest for analysis, and may complicate the analysis. Thus, it can be useful to deplete a sample of non-target RNA. It is to be understood that rRNA depletion is very important for quality of sequencing data, because rRNAs and regulatory RNAs are responsible for 95% to 98% of sequencing reads. Any RNA that does not need to be sequenced can be depleted, including ribosomal RNAs, tRNAs, regulatory RNAs and introns. The rRNA depletion works by hybridizing RNA samples to probes antisense to the RNA to be depleted, where the antisense probes include a capture moiety that can be captured by a specific binding agent. In some examples, depleting the samples of non-target RNA comprises using one or more probes that specifically hybridize to the non-target RNA, wherein the one or more probes comprise a label that facilitates removal of the probe from the sample.

In some examples the one or more probes is a plurality of probes, wherein probes in the plurality are selected to tile across the sequence of the non-target RNA. In some examples, the label comprises biotin. In some examples, the probes are biotinylated antisense probes that deplete ribosomal RNAs (18S, 28S 5.8S and 5S) and regulatory RNAs, like snRNAs. The probe-RNA is later bound to streptavidin beads to physically remove the target RNAs from the solution. Due to the GC-rich sequence of 28S, it is better to use not only biotinylated UTP, but also biotinylated CTP.

In some embodiments, the reverse transcription primers are removed and/or degraded. In some embodiments, the RNA is removed and/or degraded after first strand synthesis of ssDNA. In some examples, samples are cleaned using Silane beads to remove adaptors that did not ligate. The RNA samples can be pooled in one of several pools during the clean up step. Pools can later be coded separately, allowing even deeper multiplexing. The cleaning of samples can be performed using Silane beads or other beads such as solid phase reversible immobilization (SPRI) beads. Using beads for the clean up allows for use of robotics for the entire process thereby reducing labor cost.

In some examples, the samples of different origins comprise samples of the same cell type and/or tissue type exposed to different environmental conditions. In some examples the different environmental conditions are contact with different test agents, for example to look at the effect of such different conditions on the content of the RNA in the samples.

In some embodiments, the target RNA is mRNA, and differences in expression of the mRNA are measured across samples from different sources. In some embodiments, the sequenced target RNAs of samples from multiple sources are quantified. In some embodiments, the sequenced target RNAs are sorted to their respective sources.

There are numerous applications for the disclosed methods. Any application requiring high throughput sequencing of many eukaryotic or prokaryotic RNAs is particularly suited for the disclosed method. These include, but are not limited to, chemical screens of cell cultures to determine drugs of interest. Another use for the disclosed method is RNA/DNA targeting screens such as siRNA/shRNA. The disclosed method can be used for tissue, blood and other biological sample bank screening. In addition, the disclosed method can be used for screening RNA from paraffin block cells or tissues. The disclosed method can be used for microbiome screening. Also, the disclosed method can be used for antibiotic screening of microorganisms to determine antibiotic resistance. Expression profile screening can be performed using the disclosed method.

Appropriate samples for use in the methods disclosed herein include any conventional biological sample obtained from an organism or a part thereof that includes RNA to be analyzed, such as a plant, animal, bacteria, and the like. In particular embodiments, the biological sample is obtained from an animal subject, such as a human subject. A biological sample is any solid or fluid sample obtained from, excreted by or secreted by any living organism, including without limitation, single celled organisms, such as bacteria, yeast, protozoans, and amebas among others, multicellular organisms (such as plants or animals, including samples from a healthy or apparently healthy human subject or a human patient affected by a condition or disease to be diagnosed or investigated, such as cancer). For example, a biological sample can be a biological fluid obtained from, for example, blood, plasma, serum, urine, bile, ascites, saliva, cerebrospinal fluid, aqueous or vitreous humor, or any bodily secretion, a transudate, an exudate (for example, fluid obtained from an abscess or any other site of infection or inflammation), or fluid obtained from a joint (for example, a normal joint or a joint affected by disease, such as a rheumatoid arthritis, osteoarthritis, gout or septic arthritis). A sample can also be obtained from any organ or tissue (including a biopsy or autopsy specimen, such as a tumor biopsy) or can include a cell (whether a primary cell or cultured cell) or medium conditioned by any cell, tissue or organ. Exemplary samples include, without limitation, cells, cell lysates, blood smears, cytocentrifuge preparations, cytology smears, bodily fluids (e.g., blood, plasma, serum, saliva, sputum, urine, bronchoalveolar lavage, semen, etc.), tissue biopsies (e.g., tumor biopsies), fine-needle aspirates, and/or tissue sections (e.g., cryostat tissue sections and/or paraffin-embedded tissue sections). In other examples, the sample includes circulating tumor cells (which can be identified by cell surface markers). In particular examples, samples are used directly (e.g., fresh or frozen), or can be manipulated prior to use, for example, by fixation (e.g., using formalin) and/or embedding in wax (such as formalin-fixed paraffin-embedded (FFPE) tissue samples). It will appreciated that any method of obtaining tissue from a subject can be utilized, and that the selection of the method used will depend upon various factors such as the type of tissue, age of the subject, or procedures available to the practitioner. Standard techniques for acquisition of such samples are available. See, for example Schluger et al., *J. Exp. Med.* 176:1327-33 (1992); Bigby et al., *Am. Rev. Respir. Dis.* 133:515-18 (1986); Kovacs et al., *NEJM* 318: 589-93 (1988); and Ognibene et al., *Am. Rev. Respir. Dis.* 129:929-32 (1984).

Kits

A kit is provided for parallel sequencing target RNA from samples from multiple sources while maintaining source identification of nucleic acid probes and other reagents disclosed herein for use in the disclosed invention. In such a kit, an appropriate amount of one or more of the nucleic acid adaptors is provided in one or more containers or held on a substrate. A nucleic acid adaptor may be provided suspended in an aqueous solution or as a freeze-dried or lyophilized powder, for instance. The container(s) can be any conventional container that is capable of holding the supplied form, for instance, microfuge tubes, ampoules, or bottles. The kits can include either labeled or unlabeled nucleic acid probes. The amount of nucleic acid probe supplied in the kit can be any appropriate amount, and may depend on the target market to which the product is directed. The kit for parallel sequencing target RNA from samples from multiple sources while maintaining source identification comprises a first nucleic acid adaptor for labeling, at the 3' end, the RNA from the two or more sources that comprises a nucleic acid sequence that differentiates between the RNA from the two or more sources and a second nucleic acid adaptor for end labeling the 3' end of single stranded DNA, wherein the second nucleic acid adaptor comprises a site for binding of a PCR primer.

The following examples are provided to illustrate certain particular features and/or embodiments. These examples should not be construed to limit the invention to the particular features or embodiments described.

EXAMPLES

Example 1

The following protocol is used as a non-limiting example of the methods disclosed herein. While specific times and reagents are specified, it is contemplated that different, albeit similar reagents, times, and temperatures can be employed by those of ordinary skill in the art with minimal experimentation, given the guidance presented herein.

Multiplexing version: The first 9 nucleotides of the first read will contain a barcode (reverse & complement), where the $9^{th}$ nucleotide will always be the same for each barcode (A/T).

Each sample in the single pool has the same molarity. A Bravo robot or 96-well pipettor could be used for 48-96 samples.

Use selected RNA or upto 250 ng of total RNA/sample.

Fragment and dephosphorylate RNA samples with FastAP and PNK.

Step A. First Ligation (RNA/RNA or RNA/DNA) 3' Linker Ligation

Mix RNA+adapter+DMSO. Heat at 70° C. for 2 min→put on ice

Perform reaction as follows:

| Ligation Mix | 1 tube | N tubes |
|---|---|---|
| Dephosphorylated RNA, 5 ng | 5.5 (6) µl | 70 C. |
| Barcoded adapter/linker, 100 pmoles | 1 µl | 2 min → ice |
| DMSO (100%) | 1 µl | |
| Add master-mix | | |
| 10 × NEB ligase 1 Buffer | 2 µl | |
| DMSO (100%) | 0.8 µl | |
| ATP (100 mM) (fresh from −80° C.) | 0.2 µl | |
| PEG 8000 (50%) | 8 µl | |
| RNase inhibitor | 0.3 µl | |
| T4 RNA Ligase 1, HiConc, 36 Units | 1.2 µl | |
| Total | 20 µl | |

NOTE:
use less barcoded adapter for small amounts of RNA. T4 RNA Ligase 1, HiConc - custom NEB order, 30 U/µl Mix well many times or pipette using low-retention tips. Incubate at 23° C. for 1 hour 30 minutes.

Step B. Silane barcoded adapter cleanup:

Take 15 µl of Silane beads/sample, rinse with RLT buffer, and remove all supernatant from the beads. Bind ligation reaction with 3× volume of freshly added RLT and 0.5× (RNA+RLT volume) EtOH. Mix well. Wash beads in 123 µl of 70% EtOH twice off of magnet. Place on magnet and discard supernatant. Pool samples during second 70% ethanol wash. You can pool 4-96 samples per pool. Let air-dry at room temperature for 3-10 minutes Elute in 100-200 µl H$_2$O (no depletion protocol) or 25-90 µl H$_2$O (rRNA depletion protocol) and re-concentrate your sample with a Zymo column or Silane. Elute in 14 µl H$_2$O (no depletion protocol, go to RT directly). Continue to Step C. NOTE: For a large number of samples, the Zymo RNA concentrator kit can be used for the entire cleanup instead of Silane beads, which will reduce time and cost.

Step C (Optional). Perform oligo-based rRNA depletion after RNA-adapter ligation when needed. Use 10× rRNA probes mix (18 s+28 s+5.8 s+5 s+other regulatory RNAs) with your sample (500 ng of rRNA probe mix for 50 ng of input). Hybridize in large tubes. Heat Denature RNA+ probes at 72° C. for 2 minutes. Make a 50 µl reaction mix, consisting of:

| | |
|---|---|
| RNA oligos mix (500 ng) | 2 µl |
| 2 × Hyb Buffer (heated to 72 C.) | 25 µl |
| Ligated RNA + Adapter (100 ng) | 23 µl |
| Total (scale up if needed) | 50 µl |

Bind at 70° C. for 40 min in ThermoMixer with shaking. Prepare Streptavidin Beads after 30 minutes of incubation. Mix beads well, take 12 µl of Streptavidin beads per pool (around 40 µl/4 µg of used rRNA probes.). Place beads on magnet, remove supernatant. Wash the beads in 50 µl of Hybridization Buffer. Wash beads in 100 µl of solution A for 2 min. Wash beads in 100 µl of solution B. Wash beads in 100 µl of 1× Hybridization Buffer. Repeat a few times. Resuspend beads in 10 µl of 1× Hybridization Buffer using in shaking ThermoMixer (70° C.).

Probe removal (Binding rRNA hybrids to beads): Add pre-warmed streptavidin beads to hybridization reaction. Incubate at 68° C. for 15 min on ThermoMixer. Quickly place on the magnet; quickly transfer ALL Supernatant (which contains rRNA depleted sample) to fresh tube.

Silane sample cleanup of rRNA depleted sample: Take 20 µl of Silane beads/sample, add some RLT, remove all supernatant from the beads. Bind with 3× volume of freshly added RLT and 1× (RNA+RLT volume) EtOH, mix well. Wash beads in 123 ul of 70% EtOH twice off the magnet, Place on magnet and discard supernatant. Let air-dry at RT for 3-10 minutes. Elute 14 µl H$_2$O Estimate that the RT primer will be in at least 5× excess over the adapter leftovers. Table for estimation, real data:

| EtOH | % Adapter left |
|---|---|
| 0.4x | 1.7% |
| 0.5x | 2.5% |
| 1.5x | 25% |

Step D. First Strand cDNA synthesis

Take all 13.5 µl of RNA (eluted in 14 µl of H$_2$O). Add 1 µl of AR2 RT primer (20 µM stock, 10-50 pmoles). Mix well. Heat the mixture to 70° C. for 2 min and immediately place on ice. Add master-mix (on ice):

| AffinityScript RT Mix | 1 Reaction |
|---|---|
| 10 × RT Buffer | 2 µl |
| 100 mM DTT | 2 µl |
| 25 mM dNTP Mix | 0.8 µl |
| RNAse inhibitor | 0.4 µl |
| AffinityScript RT Enzyme | 0.8 µl |
| Total | 20 µl |

Close stripes, shake in hands, spin 5 sec—put in HOT (55° C.) incubator. Incubate at 55° C. for 55 min.

Step E. RT primer removal after Reverse Transcription using ExoSAP-IT. Add 3 µl of ExoSAP-IT into 20 µl of RT reaction and incubate at 37° C. for 12 min.

Step F. RNA degradation after RT:

Add 1 µl of 0.5M EDTA. Add 10% (2.4 µl) of 1M NaOH. Incubate at 70° C. for 12 minutes. After this, neutralize with 4.8 µl l of 0.5M Acetic Acid.

Step G. cDNA Silane cleanup. Use 12 µl of beads/sample, add some RLT to the beads, remove all supernatant. Bind with 3× volume of fresh RLT (with beads) and 0.6× (RNA+ RLT volume) EtOH, mix well. Wash beads in 123 ul of 70% EtOH twice. Place on magnet and discard supernatant. Let air-dry at RT for 3-10 minutes. Add 5.5 µl of H₂O or low TE buffer to the beads (Some water will evaporate) and keep the sample on the beads.

Step H. Second ligation (ssDNA/ssDNA) 3' Linker Ligation on the beads cDNA+adapter—heat at 75° C. for 2 min and put on ice (see below). Perform reaction as follows:

| Ligation Mix | 1 tube | |
| --- | --- | --- |
| cDNA | 5 (5.5) | 75 C. |
| 3Tr3 adapter, 100 pmoles | 1 | 2 min → ice |
| Add master-mix | | |
| 10 × NEB ligase 1 Buffer | 2 µl | |
| DMSO (100%) | 0.8 µl | |
| ATP (100 mM) (from −80° C.) | 0.2 µl | |
| PEG 8000 (50%) | 10 µl | |
| T4 RNA Ligase 1, HiC, 45 Units | 1.6 µl | |
| Total | 20 µl | |

Mix well pipetting several times, using low-retention tips. Incubate at 23° C. for 2-4 hours or overnight.

Step I. Ligated cDNA+adapter Silane Linker cleanup. Take extra 5 µl of Silane beads/sample, rinse with RLT, remove supernatant. Bind with 3× volume of fresh RLT and 0.5× (RNA+RLT volume) EtOH, mix well. Wash beads in 123 µl of 70% EtOH twice. Place on magnet and discard supernatant. Let air-dry at RT for 3-10 minutes. Elute in 27 µl H₂O.

Step J. PCR Enrichment. Make a mix consisting of:
PCR Mix for 1 Reaction (total of 50 µl ):

| cDNA | 23 µl |
| --- | --- |
| Primer 1 (2P_univ, 25 µM) | 1 µl |
| Primer 2 (2P_barcode, 25 µM) | 1 µl |
| Phusion or Q5 2 × MasterMix | 25 µl |

Run using PCR program:

| 98° C. | 30 Sec | |
| --- | --- | --- |
| 98° C. | 15 sec | |
| 67° C. | 30-60 sec | 4 cycles |
| 72° C. | 30-60 sec | |
| 98° C. | 12 sec | |
| 72° C. | 1 min | 6-10 cycles |
| 72° C. | 2 min | |

Use 8-10 cycles if you started from 10-100 ng of poly-A RNA (no depletion protocol). Use more cycles if you used 50-100 ng of RNA and depleted rRNAs or used 0.01-5 ng of poly-A RNA or RNA without depletion.

Step K. SPRI Library cleanup: Use 50 µl of SPRI beads/sample. Add SPRI beads, mix well many times with slow pipetting. Allow to sit for 2-15 min. Put on magnet, wait a few minutes. Remove supernatant. Wash beads twice with 70% Ethanol. Dry beads for 2-5 minutes, elute in 21 µl of H₂O. Load 1 µl on Bioanalyzer (Agilent) for library analysis and quantification.

Reagents List:
All additives (ATP, DTT, DMSO, dNTPs, etc.) must be stored in aliquots at −80° C. Non-perishable buffers can be store in a −25° C. freezer.

10× T4 RNA Ligase Reaction Buffer: NEB catalog #B0216B-AS

T4 RNA ligase 1, 3× high concentration, 30 U/µL, catalog #M0204B-AS RNAse inhibitor, Murine (NEB)

ATP, 100 mM, Roche (Broad SQM) (keep in single-use aliquots at −80° C.)

PEG8000, 50% in H₂O, Sigma 83271-100ML-F

DMSO HYBRI-MAX, in vials endotoxin free, D2650, Sigma

RLT buffer—Qiagen
RT set:
10× RT Buffer from Agilent for AffinityScript
100 mM DTT from Agilent or Affimetrix
dNTPs (25 mM each) from NEB or Agilent
AffinityScript Multiple-Temperature Reverse Transriptase from Agilent (any RNAseH-minus RT)
RNAse inhibitor, Murine (NEB)
After RT treatments:
ExoSAP-it—Affymetrix
0.5M EDTA, NaOH, Acetic Acid—any ultra-clean.

Example 2

RNA Depletion Protocol

Step A. Oligo-based rRNA depletion after RNA+adapter ligation.

Make your anti-sense RNA probes using both bio-UTP and bio-CTP (1:5 ratio for each=bio-UTP/UTP and bio-CTP/CTP).

Probe generation mix: Total=50 µl: H₂O=22.4 µl, NEB T7 buffer=5 µl

DNA=500-1000 ng=10 µl 100 mM ATP=1 µl, 100 mM GTP=1 µl, 100 mM CTP=0.8 µl 100 mM UTP=0.8 µl, 10 mM bio-UTP=2 µl, 10 mM bio-CTP=2 µl RNAse inhibitor=1 µl, T7 enzyme mix=4 µl Incubate 2-15 hours at 37 C. Add TurboDNAse, FastAP, clean with high-capacity RNA columns, like RNEasy (Qiagen).

Step B. Oligo-based rRNA depletion Hybridization. Use 10× rRNA probes mix (18 s+28 s+5.8 s+5 s+other regulatory RNAs=1×+2.35×+0.25×+0.2×+0.2×) with your sample (500 ng of rRNA probe mix for 50 ng of input):

| # | ratio | µg | µL | conc |
| --- | --- | --- | --- | --- |
| m18s | 1.2 | 12 | 20 | 0.6 |
| m28s₁ | 2.9 | 29 | 66 | 0.44 |
| 28sL | 0.3 | 3 | 6 | 0.5 |
| 5.8s | 0.3 | 3 | 8 | 0.36 |
| 5s | 0.2 | 2 | 3.3 | 0.6 |
| 45s | 0.31 | 3 | 7.2 | 0.43 |
| rRNA spacers | 0.31 | 3 | 7.4 | 0.42 |
| U3B | 0.21 | 2.1 | 4.5 | 0.47 |
| U1B | 0.1 | 1 | 1.7 | 0.59 |
| U3A | 0.1 | 1 | 2.2 | 0.45 |
| U2 | 0.1 | 1 | 2.3 | 0.44 |
| U5 | 0.05 | 0.5 | 2 | 0.24 |
| H₂O = 173 | | 60.7 | 130.6 | 200 ng/µL |

Hybridize in large tubes. Heat Denature RNA+probes at 72° C. for 2 min.

| RNA probe mix (500 ng) | 2 µl |
| --- | --- |
| 2 × Hyb Buffer (heated to 72° C.) | 25 µl |
| Ligated RNA+Adapter (100 ng) | 23 µl |
| Total | 50 µl |

Bind at 70° C. for 40 min in ThermoMixer with shaking. Prepare Streptavidin Beads after 30 minutes of incubation. Mix beads well, take 12 μl of Streptavidin beads per pool (around 40 μl/4 μg of used rRNA probes.). Place beads on magnet, remove supernatant. Wash the beads in 50 μl of 1× Hybridization Buffer. Wash beads in 100 μl of solution A for 2 min. Wash beads in 100 μl of solution B. Wash beads in 100 μl of 133 Hybridization Buffer. Repeat a few times. Resuspend beads in 10 μl of 1× Hybridization Buffer using shaking ThermoMixer (70° C.).

Probe removal (Bind Hybrids to beads): Add all of hot (70° C.) Streptavidin Beads to hybridization reaction. Incubate at 68° C. for 15 min on ThermoMixer. Quickly place on the magnet and quickly transfer ALL Supernatant (which contains rRNA depleted sample) to fresh tube.

Silane sample cleanup of rRNA depleted sample: Take 20 μl of Silane beads/sample, add some RLT, remove all supernatant from the beads. Bind with 3× volume of fresh RLT and 1× (RNA+RLT) volume of EtOH, mix well. Wash beads in 123 ul of 70% EtOH twice out of magnet, Place on magnet and discard supernatant. Let air-dry at RT for 3-10 minutes. Elute depleted sample from beads using water rRNA Depletion Hybridization Buffer:

| 1 × LiCl Lysis Buffer | Final (M or %) | Stock (M or %) | 1 × (mL) |
| --- | --- | --- | --- |
| 20 mM Tris-HCl (pH 7.5) | 0.02 | 1M | 0.2 |
| 5 mM EDTA | 0.005 | 0.5M | 0.1 |
| 500 mM LiCl | 0.5 | 8M | 0.625 |
| 0.25% Triton X-100 | 0.25% | 10% | 0.25 |
| 0.1% SDS | 0.1 | 20% | 0.05 |
| 0.1% Na-Deoxycholate | 0 | 4 | 0 |
| H$_2$O up to 10 ml total | | | 10 ml |

In view of the many possible embodiments to which the principles of our invention may be applied, it should be recognized that illustrated embodiments are only examples of the invention and should not be considered a limitation on the scope of the invention. Rather, the scope of the invention is defined by the following claims. The disclosed method is defined by the following claims as our invention and all that comes within the scope and spirit of this disclosure.

We claim:

1. A kit for parallel sequencing target RNA from samples from multiple sources while maintaining source identification, comprising:
    a plurality of sets;
    the plurality of sets comprising a first and second stranded nucleic acid adaptor;
    each first and second adaptor in an individual set comprising a phosphorylated 5' end;
    each first adaptor comprising a barcode sequence that is the same for all first adaptors in the set, but different for first adaptors in any other set; and a blocked 3' end, wherein each first adaptor is capable of ligation to the 3' end of the target RNA and capable of differentiating between the target RNA from the multiple sources; and
    each second adaptor comprising a site for binding of a PCR primer that is the same for all second adaptors; and a blocked 3' end, wherein each second adaptor is capable of ligation to the 3' end of single stranded DNA.

2. The kit of claim 1, wherein the second nucleic acid adaptors in the plurality of sets comprise a sequencing adaptor.

3. The kit of claim 1, wherein the second nucleic acid adaptors in the plurality of sets comprise a second barcode sequence that can differentiate between single-stranded DNA from two or more sources.

4. The kit of claim 1, wherein the first nucleic acid adaptors in the plurality of sets comprise a sequencing adaptor.

5. The kit of claim 1, further comprising one or more probes that specifically hybridize to non-target RNA, wherein the one or more probes comprise a label that facilitates removal of the probe from the sample.

6. The kit of claim 5, wherein the one or more probes are selected to hybridize to more than one sequence of each non-target RNA.

7. The kit of claim 6, wherein the label comprises biotin.

8. The kit of claim 1, wherein the first nucleic acid adaptors in the plurality of sets comprise RNA, DNA or a RNA-DNA hybrid.

9. The kit of claim 1, wherein the second nucleic acid adaptors in the plurality of sets comprise RNA, DNA or a RNA-DNA hybrid.

10. The kit of claim 1, wherein the barcode sequence is at least two nucleotides in length.

11. The kit of claim 3, wherein the second barcode sequence is at least two nucleotides in length.

\* \* \* \* \*